United States Patent
Magara et al.

[11] Patent Number: 5,973,000
[45] Date of Patent: Oct. 26, 1999

[54] HAIR REVITALIZATION TONIC COMPOSITION CONTAINING A LIPID DERIVATIVE AND USE THEREOF

[75] Inventors: Tsunao Magara, Tokyo; Yoshiharu Tsuji, Atami; Chika Hamada, Hachioji; Yosuke Nakazawa, Yokohama; Eriko Takeoka, Tokyo; Masahiro Tajima, Yokohama; Masazumi Watanabe, Kawanishi, all of Japan

[73] Assignees: Shiseido Company, Ltd., Tokyo; Takeda Chemical Industries, Ltd., Osaka, both of Japan

[21] Appl. No.: 08/867,823

[22] Filed: Jun. 3, 1997

[30] Foreign Application Priority Data

Jun. 3, 1996 [JP] Japan .................................. 8-160499

[51] Int. Cl.$^6$ .................................................. A61K 31/27
[52] U.S. Cl. ........................... 514/476; 514/478; 514/483; 514/484; 514/667; 514/668; 514/669; 514/670; 514/672; 514/238.2; 514/357; 514/371; 514/426; 514/880
[58] Field of Search ................................ 514/238.2, 357, 514/371, 426, 476

[56] References Cited

U.S. PATENT DOCUMENTS

| | | | |
|---|---|---|---|
| 2,937,119 | 5/1960 | Berger | 167/65 |
| 3,344,170 | 9/1967 | Strycker | 260/482 |
| 4,255,310 | 3/1981 | Oppenlaender et al. | 260/29.6 |
| 4,737,518 | 4/1988 | Nomura et al. | 514/476 |
| 5,089,269 | 2/1992 | Noda et al. | 424/456 |
| 5,185,334 | 2/1993 | Solomon et al. | 514/236.2 |
| 5,354,510 | 10/1994 | Vanlerberghe et al. | 252/548 |
| 5,371,252 | 12/1994 | Zysman et al. | 554/109 |
| 5,431,905 | 7/1995 | Zysman et al. | 424/70.8 |

FOREIGN PATENT DOCUMENTS

| | | |
|---|---|---|
| 142 333 | 5/1985 | European Pat. Off. . |
| 157 609 | 10/1985 | European Pat. Off. . |
| 254 540 | 1/1988 | European Pat. Off. . |
| 301 751 | 2/1989 | European Pat. Off. . |
| 0 420 761 A1 | 4/1991 | European Pat. Off. . |
| 0 577 506 A1 | 1/1994 | European Pat. Off. . |
| 1-104036 | 3/1988 | Japan . |
| 89/07100 | 8/1989 | WIPO . |

OTHER PUBLICATIONS

CAS 113:59773, Okano et al., Feb. 7, 1990.
CAS 119:203999, Belgacem et al., 1993.
CA 113:197680, Mori et al. abstract of JP02–129110, May 17, 1990.

*Primary Examiner*—Rebecca Cook
*Attorney, Agent, or Firm*—Wenderoth, Lind & Ponack, L.L.P.

[57] ABSTRACT

The invention relates to a hair revitalizing tonic composition containing, as an active ingredient, at least one lipid derivative of the general formula

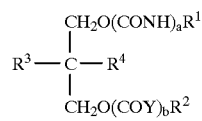

wherein $R^1$, $R^2$, $R^3$, $R^4$ and Y are as defined in the specification, and a and b are 0 or 1, as well as its use. Thus, there is provided a hair revitalizing tonic composition having an excellent hair loss prevention and hair revitalizing effect and, moreover, an excellent dandruff and itchy scalp prevention effect.

9 Claims, No Drawings

HAIR REVITALIZATION TONIC COMPOSITION CONTAINING A LIPID DERIVATIVE AND USE THEREOF

BACKGROUND OF THE INVENTION

This invention relates to hair revitalizing tonic compositions containing a specific lipid derivative as an active ingredient. The hair revitalizing tonic compositions of this invention are particularly intended for use in at least one technical field of application selected from drugs, quasi drugs and cosmetics.

Conventionally, the causes of baldness and hair loss have been considered to be disorders of the scalp resulting from the activation of male hormones in organs such as hair roots and sebaceous glands, an insufficient circulation of blood to hair follicles, an excessive secretion of sebum, the formation of peroxides, and the like. Accordingly, compounds or compositions having the effect of removing or alleviating the above-described causes are usually incorporated in conventional hair revitalizing tonic compositions.

These compounds or compositions include, for example, vitamins such as vitamin B complex and vitamin E; amino acids such as serine and methionine; vasodilators such as swertia herb extract, benzyl nicotinate and acetylcholine derivatives; anti-inflammatory agents such as lithospermum root extract and hinokitiol; female hormones such as estradiol; and skin function promoters such as cepharanthine. Actually, some of them are being used in the prophylaxis and treatment of alopecia.

However, in spite of the above-described various attempts which have been made, conventional hair revitalizing tonic compositions do not always exhibit satisfactory hair revitalizing effects such as hair loss prevention and hair generation effects. Presumably, the reason for this is believed to be that the cause of hair loss is varied and the mechanism of hair generation is highly complicated.

Thus, there is a continuing need for a hair revitalizing tonic composition which has an excellent hair loss prevention and hair revitalizing effect and, moreover, is effective in preventing dandruff and an itchy scalp.

SUMMARY OF THE INVENTION

In order to accomplish the above-described need, the present inventors have made investigations on the hair revitalizing effects of a wide variety of compounds and compositions and have now found that certain lipid derivatives, most of which are known compounds (see EP 157609A, Japanese Patent Laid-Open No. 104036/1989, EP 301751A, EP 142333A, WO 89/07100 and EP 254540A), have a powerful hair revitalizing effect.

Accordingly, the present invention provides a hair revitalizing tonic composition containing, as an active ingredient, at least one compound of the following general formula (I) or a salt thereof, a hair revitalizing method, and the use of the aforesaid compound or a salt thereof in the preparation of a hair revitalizing tonic composition.

General formula (I):

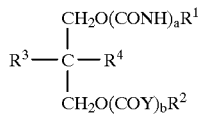

wherein $R^1$ and $R^2$ are each independently a $C_{1-30}$ hydrocarbon radical which may be substituted, or a five-or six-membered heterocyclic group which contains 1 to 4 heteroatoms selected from oxygen, sulfur and nitrogen atoms and which may be substituted, $R^3$ and $R^4$ are each independently hydrogen, hydroxyl or a $C_{1-4}$ alkoxy group, Y is an imino group which may be substituted, a is 0 or 1, and b is 0 or 1.

When the carbon atom to which $R^3$ and $R^4$ are joined has asymmetry, or when an asymmetrical carbon atom is present in any of the $R^1$ or $R^2$ groups, the compound of formula (I) can be any one of its optically active forms or a mixture thereof.

DETAILED DESCRIPTION OF THE INVENTION

The term "hair revitalization" as used herein comprehends, in its broad sense, the promotion of hair growth, the stimulation of hair growth, and the prevention of hair loss in mammals including man, as well as the prevention of an itchy scalp, the prevention of dandruff, and the like.

In the compounds of the above formula (I), $R^1$ and $R^2$ are each independently a $C_{1-30}$ alkyl group, a $C_{3-8}$ cycloalkyl group, a $C_{2-10}$ alkenyl group, a $C_{2-10}$ alkynyl group, a $C_{3-10}$ cycloalkenyl group, a $C_{6-14}$ aryl group or a $C_{7-16}$ aralkyl group, which may be substituted; when these groups are substituted, 1 to 5 substituents may be present at a substitutable position or positions, and these substituents may be selected from the class consisting of $C_{3-8}$ cycloalkyl, hydroxyl, oxo, thioxo, cyano, carbamoyl, carboxyl, $C_{1-4}$ alkoxycarbonyl, sulfo, halogen, $C_{1-4}$ alkoxy, phenoxy, halogenophenoxy, $C_{1-4}$ alkylthio, phenylthio, $C_{1-4}$ alkylsulfinyl, $C_{1-4}$ alkylsulfonyl, amino, $C_{1-6}$ acylamino, $C_{1-30}$ alkylamino, di-$C_{1-30}$ alkylamino, quaternized groups derived from these amino and substituted amino groups, $C_{1-4}$ acyl, benzoyl, five- or six-membered heterocyclic groups which contain 1 to 4 heteroatoms selected from oxygen, sulfur and nitrogen atoms in addition to carbon atoms and which may be substituted (when they are substituted, there may 1 to 4 substituents selected from halogen, $C_{1-4}$ alkyl and halogenophenoxy), and $C_{1-10}$, haloalkyl; and when $R^1$ and $R^2$ are each a cycloalkyl group, a cycloalkenyl group, an aryl group or an aralkyl group, 1 to 4 $C_{1-4}$ alkyl groups may be present at a substitutable position or positions in the ring.

In the compounds of the above formula (I), when the carbon atom to which $R^3$ and $R^4$ are joined has asymmetry, these compounds have two stereoisomers having the R- and S-configurations. In such a case, the compounds usable as active ingredients according to the present invention can exist in the form of each of these stereoisomers, a racemate thereof, or a mixture thereof. In the present invention, besides mixtures of the aforesaid stereoisomers, the compounds in which at least one of $R^1$, $R^2$, $R_3$, $R^4$, a and b has different meanings may be used in admixture of two or more.

The compounds of the above formula (I) exhibit, among others, a hair loss prevention effect and a hair growth promotion or stimulation effect when applied to the human skin and, in particular, the scalp or hair. Moreover, they also have the effect of suppressing dandruff production and an itchy scalp.

The compounds of formula (I) which are contained as active ingredients in the hair revitalizing tonic compositions of the present invention are more specifically described hereinbelow.

Where $R^1$ in formula (I) represents a $C_{1-30}$ alkyl group which may be substituted, examples thereof include straight-chain alkyl groups such as methyl, ethyl, butyl, pentyl, hexyl, heptyl, octyl, nonyl, decyl, undecyl, dodecyl, tridecyl, tetradecyl, pentadecyl, hexadecxyl, heptadecyl, octadecyl, nonadecyl, icosyl, henicosyl, docosyl, tricosyl, tetracosyl, pentacosyl, hexacosyl, heptacosyl, octacosyl, nonacosyl and triacontyl; and branched alkyl groups such as isopropyl, isobutyl, s-butyl, t-butyl, 2-methylpentyl, 3-methylpentyl, 4-isocapryl, 4-ethylpentyl, 6-methyldecyl, 9-methyldecyl, 6-ethylnonyl, 5-propyloctyl, 11-methyldodecyl, 12-methyldodecyl, 4-methyltetradecyl, 13-methyltetradecyl, 14-ethylhexadecyl, 10-methyloctadecyl, 15-ethylpentadecyl, 10-methyldodecyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl, 3-methyltetracosyl and 3-methyltricosyl.

Among others, $R^1$ is preferably a straight-chain or branched $C_{6-22}$ alkyl group which may be substituted, and more preferably a straight-chain or branched $C_{8-20}$ alkyl group. The substituents present in substituted alkyl groups will be described later. For example, when such alkyl groups are substituted by a $C_{3-8}$ cycloalkyl group at the ω-position, they are preferably straight-chain $C_{6-14}$ alkyl groups.

Examples of the $C_{3-8}$ cycloalkyl group represented by $R^1$ include cyclopropyl, cyclopentyl and cyclohexyl. Examples of the $C_{2-10}$ alkenyl group represented by $R^1$ include vinyl, allyl, 2-methylallyl, 2-butenyl, 3-butenyl, 3-octenyl, 2-nonenyl and 4-decenyl. Examples of the $C_{2-10}$ alkynyl group represented by $R^1$ include ethynyl, 2-propynyl and 3-hexynyl. Examples of the $C_{3-10}$ cycloalkenyl group represented by $R^1$ include cyclopropenyl, cyclopentenyl and cyclohexenyl.

Examples of the $C_{6-14}$ aryl group represented by $R^1$ include phenyl and naphthyl. Examples of the $C_{7-16}$ aralkyl group represented by $R^1$ include benzyl and phenylethyl.

The foregoing radicals represented by $R^1$ may have one or more (e.g., one to five) substituents at any substitutable position or positions in the carbon chain or carbon ring. Specific examples of the substituents include $C_{3-8}$ cycloalkyl, hydroxyl, oxo, thioxo, cyano, carbamoyl, carboxyl, $C_{1-4}$ alkoxycarbonyl (e.g., methoxycarbonyl and ethoxycarbonyl), sulfonyl, halogen (e.g., fluorine, chlorine, bromine and iodine), $C_{1-4}$ alkoxy (e.g., methoxy, ethoxy, propoxy, isopropoxy, butoxy, isobutoxy, s-butoxy and t-butoxy), phenoxy, halogenophenoxy (e.g., o-, m- or p-chlorophenoxy and o-, m- or p-bromophenoxy), lower ($C_{1-4}$) alkylthio (e.g., methylthio, ethylthio, n-propylthio, isopropylthio, n-butylthio and t-butylthio), phenylthio, $C_{1-4}$ alkylsulfinyl (e.g., methylsulfinyl and ethylsulfinyl), $C_{1-4}$ alkylsulfonyl (e.g., methylsulfonyl and ethylsulfonyl) and $C_{1-10}$ haloalkyl (e.g., difluoromethyl, trifluoromethyl, trifluoroethyl and trichloroethyl).

Other specific examples of the substituents include amino, $C_{1-6}$ acylamino (e.g., acetylamino and propionylamino), $C_{1-30}$ alkylamino (e.g., methylamino, ethylamino, n-propylamino, isopropylamino, n-butylamino, isobutylamino, s-butylamino, t-butylamino, pentylamino, hexylamino, heptylamino, octylamino, nonylamino, decylamino, undecylamino, dodecylamino, tridecylamino, tetradecylamino, pentadecylamino, hexadecxylamino, heptadecylamino, octadecylamino, nonadecylamino, icosylamino, henicosylamino, docosylamino, tricosylamino, tetracosylamino, pentacosylamino, hexacosylamino, heptacosylamino, octacosylamino, nonacosylamino and triacontylamino), di-$C_{1-4}$ alkylamino (e.g., dimethylamino, diethylamino, N-methyl-N-ethylamino and N-methyl-N-propylamino), acyl (e.g. formyl and acetyl) and benzoyl.

Further specific examples of the substituents include five- and six-membered heterocyclic groups which contain 1 to 4 heteroatoms selected from oxygen, sulfur and nitrogen atoms and which may be substituted, such as pyrrolidyl, piperidyl, morpholino, 2- or 3-thienyl, 2-or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1, 2, 3-or 1, 2, 4-triazolyl, 1H- or 2H-tetrazolyl, 2-, 3- or 4-pyridyl, 2-, 4- or 5-pyrimidyl, 3- or 4-pyridazinyl, quinolyl, isoquinolyl and indolyl. These heterocyclic groups may have 1 to 4 substituents. Specific examples of the substituents include halogen (e.g., fluorine, chlorine and bromine), $C_{1-4}$ alkyl groups (e.g., methyl, ethyl, propyl and isopropyl) and halogenophenoxy (e.g., o-, m- or p-chlorophenoxy and o-, m- or p-bromophenoxy).

Where $R^1$ represents a cycloalkyl, cycloalkenyl, aryl or aralkyl group as described above and is substituted, it may have any of the above-described substituents, so long as the objects of the present invention are accomplished. However, it is preferable that $R^1$ has 1 to 4 substituents comprising $C_{1-4}$ alkyl groups such as methyl, ethyl, propyl, isopropyl and butyl.

The heterocyclic groups represented by $R^1$ and $R^2$ may be substituted by halogen or $C_{1-4}$ alkyl. Examples of the heterocyclic groups represented by $R^1$ and $R^2$ include the same five- and six-membered heterocyclic groups which contain 1 to 4 heteroatoms selected from oxygen, sulfur and nitrogen atoms as those mentioned above as the substituents for the hydrocarbon radicals represented by $R^1$ and $R^2$, and more preferred examples include 2-, 3- or 4-pyridyl and piperidyl.

$R^2$ in formula (I) may be the same as defined above for $R^1$. However, $R^2$ is preferably a group of the formula

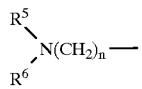

wherein $R^5$ and $R^6$ are each independently hydrogen or a $C_{1-5}$ alkyl group which may be substituted, or $R^5$ and $R^6$ are residues combined with the adjacent nitrogen atom to form a nitrogen-containing heterocyclic group (e.g., a five- or six-membered heterocyclic group, and n is an integer of 1 to 10. Specific examples of the $C_{1-5}$ alkyl group are the same as enumerated above for the case in which $R^1$ is an alkyl group.

Where Y represents an imino group which may be substituted, examples thereof include groups of the formula

wherein $R^7$ is hydrogen, alkyl which may be substituted, acyl, phenoxycarbonyl, lower ($C_{1-5}$) alkoxy carbonyl, or carbamoyl which may be substituted.

In the above formula, examples of the alkyl group represented by $R^7$ include alkyl groups of about 1 to 5 carbon atoms, such as methyl, ethyl, propyl, butyl and pentyl. These alkyl groups may be substituted, for example, with carboxyl or lower ($C_{1-5}$) alkoxycarbonyl (e.g., methoxycarbonyl, ethoxycarbonyl, propoxycarbonyl, butoxycarbonyl or pentoxycarbonyl).

Examples of the acyl group represented by $R^7$ include lower ($C_{1-5}$ or so) alkanoyl (e.g., formyl, acetyl, propionyl, butyryl, isobutyryl, valeryl and isovaleryl) and benzoyl. Examples of the lower ($C_{1-5}$) alkoxycarbonyl group represented by $R^7$ include methoxycarbonyl, ethoxycarbonyl, propoxycarbonyl, butoxycarbonyl and pentoxycarbonyl. Examples of the carbamoyl group which is represented by $R^7$ and may be substituted include carbamoyl, lower ($C_{1-5}$) alkylcarbamoyl (e.g., methylcarbamoyl, ethylcarbamoyl, propylcarbamoyl and butylcarbamoyl), di-lower ($C_{1-5}$) alkylcarbamoyl (e.g., dimethylcarbamoyl, methylethylcarbamoyl, diethylcarbamoyl and methylpropylcarbamoyl), three- to seven-membered cylic aminocarbonyl [e.g., (aziridin-1-yl)carbonyl, (azetidin-1-yl) carbonyl, (pyrrolidin-1-yl)carbonyl, piperidynocarbonyl, (perhydroazepin-1-yl)carbonyl, (piperazin-1-yl)carbonyl, morpholinocarbonyl and thiomorpholinocarbonyl].

Where the hydrocarbon radical which is represented by $R^2$ and -may be substituted is a group of the formula

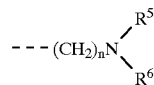

wherein $R^5$, $R^6$ and n are as defined previously, $R^7$ may be combined with $R^5$ or $R^6$ to form an alkenylene or alkylene bridge. Examples of the alkenylene or alkylene bridge include lower ($C_{1-4}$ or so) alkenylene and alkylene groups such as methylene, ethylene, trimethylene, tetramethylene, vinylene and propenylene. These groups may have one or two substitutents (e.g., oxo) at a substitutable position or positions. Examples of substituted alkylene and alkenylene groups include 1-oxo-ethylene, 3-oxopropenylene and 1,2-dioxoethylene. In this case, specific examples of the group represented by Y-$R^2$ include

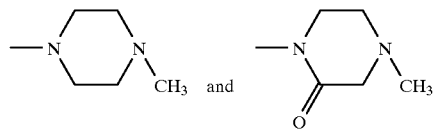

Where Y is a substituted imino group, it is preferable that the imino group is substituted by a lower alkanoyl group. More preferably. Y is an unsubstituted imino group (—NH—).

$R^3$ and $R^4$ in formula (I) are each independently hydrogen, hydroxyl, or a $C_{1-4}$ alkoxy group such as methoxy, ethoxy, propoxy or butoxy.

In formula (I), a and b are each independently 0 or 1. Accordingly, when each of a and b is 0, the compounds of formula (I) are such that $R^1$ and $R^2$ are each joined through the medium of an ether linkage. When each of a and b is 1, $R^1$ and $R^2$ are joined through the medium of an oxycarbamoyl linkage (—OCONH—) and —OCOY—, respectively. The compounds in which one of a and b is 0 and the other is 1 also fall within the scope of formula (I) and can hence be used in the present invention.

Where the compounds of formula (I) have a basic group such as amino or imino, the compounds of formula (I) can be pharmaceutically acceptable acid addition salts thereof. The term "pharmaceutically acceptable" as used herein means that, in the provision of a pharmaceutical preparation or a cosmetic preparation, no adverse influence is exerted on the properties or physiological activity of the preparation. Such salts include pharmaceutically acceptable inorganic acid salts such as hydrohalogenides (e.g., hydrochloride and hydrobromide), sulfate, nitrate and phosphate; and pharmaceutically acceptable organic acid salts such as acetate, propionate, hydroxyacetate, 2-hydroxypropionate, 2-oxopropionate, oxalate, malonate, succinate. methanesulfonate, ethanesulfonate, benzenesulfonate, 4-methylbenzenesulfonate and 2-hydroxybenzoate.

Where the compounds of formula (I) have a carboxyl group, it can also be used as ammonium salts, alkali metal salts (e.g., lithium, sodium and potassium salts), or salts with organic bases (e.g., amino acids such as arginine and lysine).

Among the foregoing compounds of formula (I) and salts thereof, compounds which can be advantageously used in the present invention are shown in Table I below, through the present invention is not limited thereto.

TABLE I

General formula (I):

(I)

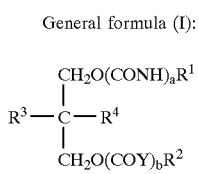

| Compound No. | $R^1$ | $R^3$ | $R^4$ | Y | $R^2$ | a | b |
|---|---|---|---|---|---|---|---|
| 1 | $C_{18}H_{37}$ | H | $OCH_3$ | NH | $(CH_2)_3N(CH_3)_2$ | 1 | 1 |
| 2 | Hydrochloride of Compound 1 | | | | | | |
| 3 | $C_{18}H_{37}$ | H | $OCH_3$ | NH | $(CH_2)_2N(CH_3)_2$ | 1 | 1 |
| 4 | Hydrochloride of Compound 3 | | | | | | |

TABLE I-continued

General formula (I):

$$R^3-\underset{\underset{CH_2O(COY)_bR^2}{|}}{\overset{\overset{CH_2O(CONH)_aR^1}{|}}{C}}-R^4 \quad (I)$$

| Compound No. | R¹ | R³ | R⁴ | Y | R² | a | b |
|---|---|---|---|---|---|---|---|
| 5 | $C_{18}H_{37}$ | H | $OCH_3$ | NH | $(CH_2)_4N(CH_3)_2$ | 1 | 1 |
| 6 | $C_{18}H_{37}$ | H | $OCH_3$ | NH | $(CH_2)_5N(CH_3)_2$ | 1 | 1 |
| 7 | $C_{18}H_{37}$ | H | $OCH_3$ | NH | $(CH_2)_6N(CH_3)_2$ | 1 | 1 |
| 8 | $C_{18}H_{37}$ | H | $OCH_3$ | NH | $(CH_2)_7N(CH_3)_2$ | 1 | 1 |
| 9 | $C_{18}H_{37}$ | H | $OCH_3$ | NH | $(CH_2)_8N(CH_3)_2$ | 1 | 1 |
| 10 | $C_{17}H_{35}$ | H | $OCH_3$ | NH | $(CH_2)_3N(CH_3)_2$ | 1 | 1 |
| 11 | $C_{16}H_{33}$ | H | $OCH_3$ | NH | $(CH_2)_3N(CH_3)_2$ | 1 | 1 |
| 12 | $C_{15}H_{31}$ | H | $OCH_3$ | NH | $(CH_2)_3N(CH_3)_2$ | 1 | 1 |
| 13 | $C_{12}H_{25}$ | H | $OCH_3$ | NH | $(CH_2)_3N(CH_3)_2$ | 1 | 1 |
| 14 | $C_8H_{17}$ | H | $OCH_3$ | NH | $(CH_2)_3N(CH_3)_2$ | 1 | 1 |
| 15 | $C_{18}H_{37}$ | H | H | NH | $(CH_2)_3N(CH_3)_2$ | 1 | 1 |
| 16 | Hydrochloride of Compound 15 | | | | | | |
| 17 | $C_{18}H_{37}$ | H | OH | NH | $(CH_2)_3N(CH_3)_2$ | 1 | 1 |
| 18 | $C_{18}H_{37}$ | H | $OC_2H_5$ | NH | $(CH_2)_3N(CH_3)_2$ | 1 | 1 |
| 19 | $C_{18}H_{37}$ | H | H | | $(CH_2)_4N(CH_3)_2$ | 0 | 0 |
| 20 | Hydrochloride of Compound 19 | | | | | | |
| 21 | $C_{18}H_{37}$ | H | H | | $(CH_2)_3N(CH_3)_2$ | 0 | 0 |
| 22 | $C_{18}H_{37}$ | H | H | | $(CH_2)_5N(CH_3)_2$ | 0 | 0 |
| 23 | $C_{18}H_{37}$ | H | H | | $(CH_2)_6N(CH_3)_2$ | 0 | 0 |
| 24 | 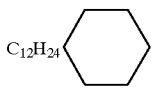 | H | $OCH_3$ | | $(CH_2)_4N(CH_3)_2$ | 0 | 0 |
| 25 | Hydrochloride of Compound 24 | | | | | | |
| 26 | 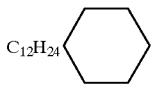 | H | $OCH_3$ | NH | $(CH_2)_3N(CH_3)_2$ | 0 | 1 |
| 27 | Hydrochloride of Compound 26 | | | | | | |
| 28 | $C_{18}H_{37}$ | H | $OCH_3$ | NH | 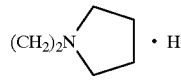 | 1 | 1 |
| 29 | $C_{18}H_{37}$ | H | $OCH_3$ | NH | 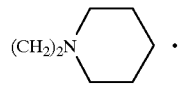 | 1 | 1 |
| 30 | $C_{18}H_{37}$ | H | $OCH_3$ | NH | 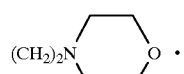 | 1 | 1 |
| 31 | $C_{18}H_{37}$ | H | OH | NH | $(CH_2)_2N(CH_3)_2$ | 0 | 1 |
| 32 | $C_{18}H_{37}$ | H | $OCH_3$ | NH | 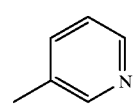 | 1 | 1 |

TABLE I-continued
General formula (I):
$$R^3-\underset{\underset{CH_2O(COY)_bR^2}{|}}{\overset{\overset{CH_2O(CONH)_aR^1}{|}}{C}}-R^4 \quad (I)$$
| Compound No. | R1 | R³ | R⁴ | Y | R² | a | b |
|---|---|---|---|---|---|---|---|
| 33 | $C_{18}H_{37}$ | H | $OCH_3$ | NH | 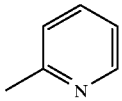 | 1 | 1 |
| 34 | $C_{18}H_{37}$ | H | $OCH_3$ | NH | 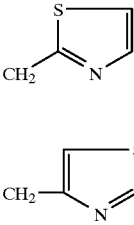 | 1 | 1 |
| 35 | $C_{18}H_{37}$ | H | $OCH_3$ | NH | 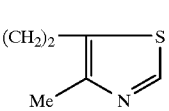 | 1 | 1 |
| 36 | $C_{18}H_{37}$ | H | $OCH_3$ | NH | 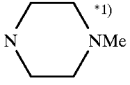 | 1 | 1 |
| 37 | $C_{18}H_{37}$ | H | $OCH_3$ |   | 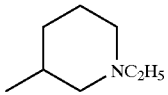 *1) | 1 | 1 |
| 38 | $C_{18}H_{37}$ | H | $OCH_3$ | NH | 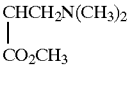 | 1 | 1 |
| 39 | $C_{18}H_{37}$ | H | $OCH_3$ | NH | $\underset{CO_2CH_3}{\overset{CHCH_2N(CH_3)_2}{|}}$ | 1 | 1 |
| 40 | $C_{18}H_{37}$ | H | H | NH | 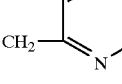 | 1 | 1 |
| 41 | $C_{18}H_{37}$ | H | $OCH_3$ |  | $(CH_2)_2N(CH_3)_2 \cdot HCl$ | 1 | 1 |
| 42 | $C_{18}H_{37}$ | H | $OCH_3$ |  | $(CH_2)_2N(CH_3)_2 \cdot HCl$ | 1 | 1 |

TABLE I-continued

General formula (I):

$$R^3-C(-R^4)(CH_2O(CONH)_aR^1)(CH_2O(COY)_bR^2) \quad (I)$$

Formula (I)

| Compound No. | R¹ | R³ | R⁴ | Y | R² | a | b |
|---|---|---|---|---|---|---|---|
| 43 | $C_{18}H_{37}$ | H | $OCH_3$ | N–COCH₃ | $(CH_2)_2$-pyrrolidinyl · HCl | 1 | 1 |
| 44 | $C_{18}H_{37}$ | H | $OCH_3$ | N–COCH₃ | $(CH_2)_2$-piperidinyl · HCl | 1 | 1 |
| 45 | $C_{18}H_{37}$ | H | $OCH_3$ | N–COCH₃ | $CH_2$-(1-ethylpyrrolidin-2-yl) · HCl | 1 | 1 |
| 46 | $C_{18}H_{37}$ | H | $OCH_3$ | N–COC₂H₅ | $(CH_2)_2N(CH_3)_2$ | 1 | 1 |
| 47 | $C_{18}H_{37}$ | H | $OCH_3$ | N–CO₂CH₃ | $(CH_2)_2N(CH_3)_2$ | 1 | 1 |
| 48 | $C_{18}H_{37}$ | H | $OCH_3$ | N–CO₂–phenyl | $(CH_2)_2N(CH_3)_2$ | 1 | 1 |
| 49 | $C_{18}H_{37}$ | H | $OCH_3$ | N–CON (pyrrolidinyl) | $(CH_2)_2N(CH_3)_2$ | 1 | 1 |
| 50 | $C_{18}H_{37}$ | H | $OCH_3$ | N–CON(CH₂)₂ | $(CH_2)_2N(CH_3)_2$ | 1 | 1 |
| 51 | $C_{18}H_{37}$ | H | $OCH_3$ | N–CONHC₃H₇ | $(CH_2)_2N(CH_3)_2$ | 1 | 1 |
| 52 | $C_{18}H_{37}$ | H | $OCH_3$ | N–COCH₃ | $CH_2$-(pyridin-2-yl) | 1 | 1 |

TABLE I-continued

General formula (I):

$$R^3-\underset{\underset{CH_2O(COY)_bR^2}{|}}{\overset{\overset{CH_2O(CONH)_aR^1}{|}}{C}}-R^4 \quad (I)$$

| Compound No. | R¹ | R³ | R⁴ | Y | R² | a | b |
|---|---|---|---|---|---|---|---|
| 53 | $C_{18}H_{37}$ | H | $OCH_3$ | 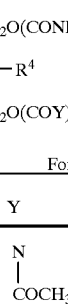 | 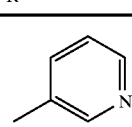 | 1 | 1 |
| 54 | $C_{18}H_{37}$ | H | $OCH_3$ |  | 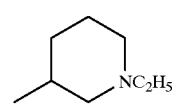 | 1 | 1 |

(Note) The reference mark (*1) given for compound 37 means that Y and R² are combined to form the indicated group.

As described above, most of the foregoing compounds of formula (I) are disclosed in EP 157609A, and they may be prepared according to the processes described in this patent and Japanese Patent Laid-Open No. 104036/1989, EP 301751A, EP 142333A, WO 89/07100 or EP 2545400A or modifications thereof.

Specifically, according to the above-described processes, compounds (I) or salts thereof may be prepared, for example, in the following manner.

A) Where $R^2$ in formula (I) is represented by the formula

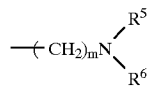

wherein m is an integer of 1 to 30 and the other symbols are as defined previously, compounds (I) can be obtained by reacting a compound (II) of the formula

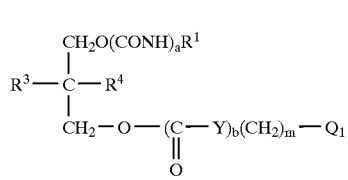

(II)

wherein $Q_1$ is a group capable of being easily replaced by nitrogen [such as halogen (e.g., chlorine, bromine or iodine), O-tosyl or O-mesyl] and the other symbols are as defined previously, with an amine (III) or nitrogen-containing cyclic compound (IV) which may be substituted. The reaction of compound (II) with compound (III) or (IV) may be carried out by adding an equivalent amount or a large excess of compound (III) or (IV) to compound (II), and reacting this mixture in the presence or absence of a solvent at a temperature of 0 to +200° C. Usable solvents include toluene, benzene, ether, dioxane, tetrahydrofuran and the like, and- compound (III) or (IV) itself may be used as the solvent. Under heated conditions, the reaction may be carried out in a sealed tube.

It is also possible to convert a compound (IIa) of the formula

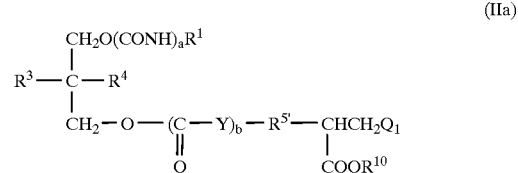

(IIa)

wherein $R^{10}$ is a lower ($C_{1-4}$) alkyl group, $R^{5'}$ is a single bond or a $C_{1-28}$ alkylene group, and the other symbols are as defined previously, into a compound (IIb) of the formula

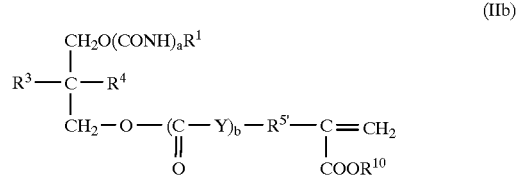

(IIb)

wherein the symbols are as defined previously, according to a per se known procedure, and then react compound (IIb) with compound (III) or (IV) in substantially the same manner as described for the reaction of compound (II) with compound (III) or (IV). Thus, there can be obtained compounds of the formula

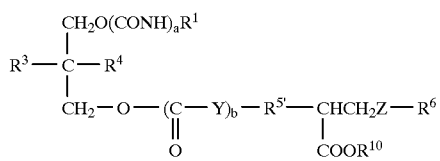

(Ia)

wherein Z is an imino or nitrogen-containing heterocyclic group which may be substituted and the other symbols are as defined previously.

B) Where b in formula (I) is 1, compounds (I) can be obtained by reacting a compound of the formula

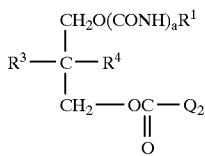

(V)

wherein $Q_2$ is a group capable of activating the carbonyl group [such as halogen (e.g., chlorine) or phenoxy] and the other symbols are as defined previously, with a compound of the formula

 (VI)

wherein the symbols are as defined previously. The reaction of compound (V) with compound (VI) may be carried out in the presence or absence of a solvent at a temperature of −10 to +150° C. Usable solvents include toluene, benzene, ether, dioxane, tetrahydrofuran, chloroform and the like, and a base such as triethylamine or pyridine may be added to accelerate the reaction. It is also possible to react compound (VI) with sodium hydride, n-butyllithium or the like in any of the above-described solvents to convert it into a metallic salt thereof, and then react this metallic salt with compound (V).

C) Compounds (I) can be obtained by reacting a compound of the formula

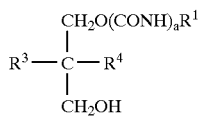

(VII)

wherein the symbols are as defined previously, with a compound of the formula

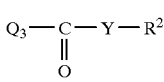

(VIII)

wherein $Q_3$ is a group capable of activating the carbonyl group [such as halogen (e.g., chlorine) or phenoxy] and the other symbols are as defined previously. The reaction of compound (VII) with compound (VIII) may be carried out in substantially the same manner as described for the reaction of compound (V) with compound (VI) in B).

D) Compounds (I) in which Y is —NH— can be obtained by reacting a compound of the formula

 (IX)

wherein the symbols are as defined previously, with a compound of formula (VII). This reaction may be carried out in substantially the same manner as described for the reaction of compound (VII) with compound (VII).

Compound (IX) may readily be synthesized, for example, by reacting a compound of the formula

 (X)

wherein the symbols are as defined previously, with diphosgene in the absence of solvent or in the presence of an inert solvent such as methylene chloride, chloroform, benzene, tetrahydrofuran or toluene, at a temperature of −20 to +120° C., or by reacting a compound of the formula

 (XI)

wherein the symbols are as defined previously, with DPPA in a solvent such as chloroform, toluene, benzene, dichloromethane or tetrahydrofuran, in the presence of a tertiary amine such as triethylamine or tributylamine, at a temperature of 0 to +150° C., and then in the presence of a tertiary amine such as pyridine, at a temperature of 0 to +150° C.

A compound of formula (Ia) in which the nitrogen atom contained in the Z group is secondary or tertiary can be obtained by reacting a compound of formula (Ia) in which the nitrogen atom contained in the Z group is primary or secondary, respectively, with an alkyl halide. This reaction may be carried out in a solvent such as ether, chloroform, tetrahydrofuran, benzene or toluene, in the presence of an equivalent amount or large excess of an alkyl halide, at a temperature of 0 to +150° C.

A compound of formula (I) in which a is 0 and $R^1$ is carbamoyl can be obtained by reacting a compound of formula (I) in which a is 0 and $R^1$ is hydrogen with an alkyl isocyanate. This reaction may be carried out in substantially the same manner as described for the reaction of compound (V) with compound (VI).

Among the starting compounds represented by the formula (II), a representative starting compound (II') shown below, may be prepared, for example, according to the following reaction formulae.

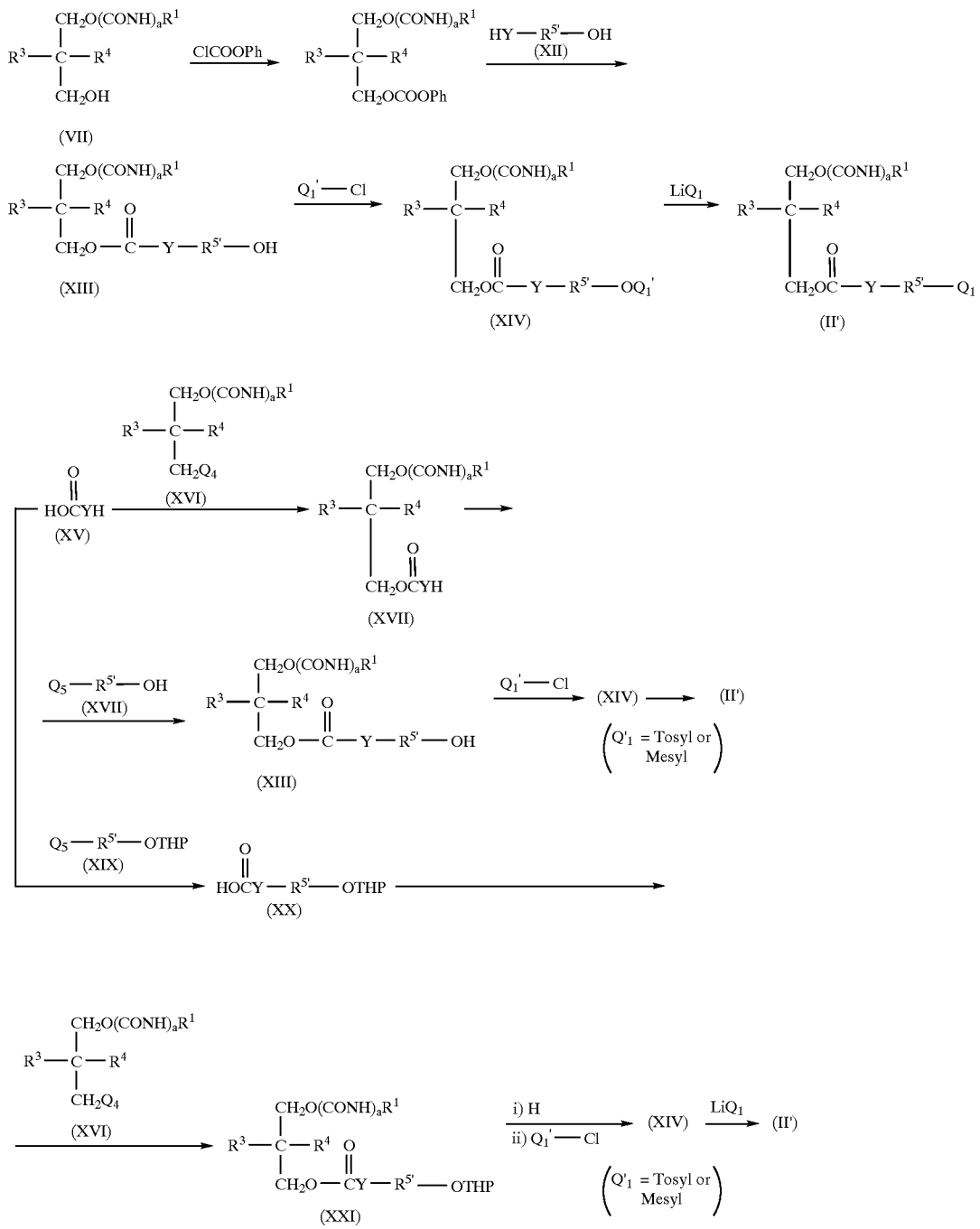

In the above formulae, $Q_1'$ is tosyl or mesyl, THP is tetrahydropyran-2-yl, $Q_4$ and $Q_5$ are each halogen (e.g., chlorine, bromine or iodine), O-tosyl or O-mesyl, and the other symbols are as defined previously.

Compounds (V) and (VIII) may be synthesized by reacting compounds (VII) and (VI), respectively, with phenyl chlorocarbonate, phosgene or diphosgene.

Compounds (VIII') represented by the formula

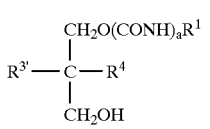

(VII')

wherein $R^{3'}$ is alkoxy or aralkyloxy and the other symbols are as defined previously, may be prepared, for example, according to the following reaction formula.

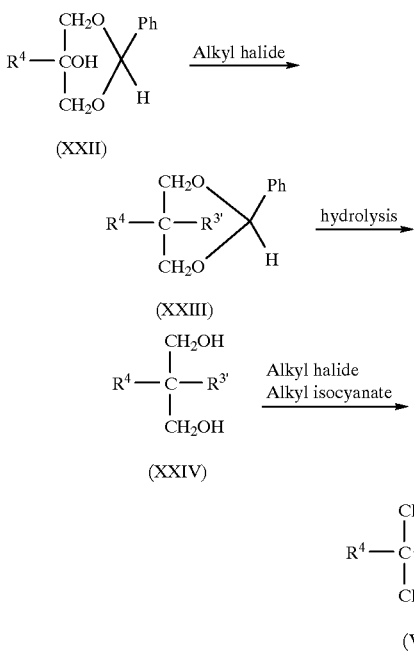

(XXII)

(XXIII)

(XXIV)

(VII')

wherein Ph is phenyl group and the other symbols are as defined previously.

Compounds (I') represented by the formula

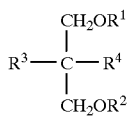

(I')

wherein the symbols are as defined previously, may be synthesized, for example, according to the following reaction formula.

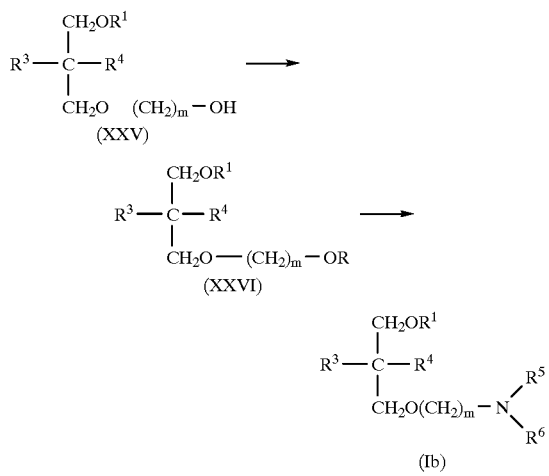

(XXV)

(XXVI)

(Ib)

wherein R is benzenesulfonyl, lower alkylbenenesulfonyl or lower alkanesulfonyl and the other symbols are as defined previously.

Compound (XXVI) can be obtained by reacting compound (XXV) with a sulfonic acid halide in a suitable anhydrous solvent (e.g., benzene, toluene, dichloromethane, chloroform, pyridine or a mixture thereof), in the presence of a suitable acid accepting base (e.g., a tertiary amine such as triethylamine or pyridine), at a temperature of −20 to +100° C. and preferably −10 to +50° C. Useful sulfonic acid halides include, for example, benezenesulfonyl halides (e.g., benzenesulfonyl chloride), lower ($C_{1-4}$) alkylbenenesulfonyl halides (e.g., toluenesulfonyl chloride) and lower ($C_{1-4}$) alkanesulfonyl chlorides (e.g., methanesulfonyl chloride).

Compound (Ib) can be obtained by reacting compound (XXVI) with an amine (III) of the formula

(III)

This reaction may be carried out in an excess of the amine or in a suitable solvent (e.g., water, methanol, ethanol, benzene, toluene, tetrahydrofuran, dimethylformamide or a mixture thereof), at a temperature of −20 to +150° C. and preferably 0 to 80° C. If necessary, this reaction may be carried out in a sealed tube at room temperature or an elevated temperature.

Alternatively, the aforesaid compound (Ib) may be prepared according to the following reaction formula.

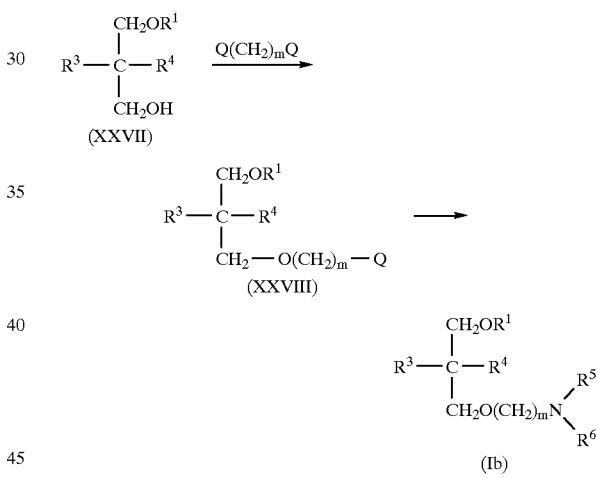

(XXVII)

(XXVIII)

(Ib)

wherein the symbols are as defined previously and Q is halogen.

Compound (XXVIII) can be obtained by reacting compound (XXVII) with a dihaloalkane of the formula

$Q(CH_2)_mQ$

This reaction may be carried out in the absence of solvent or in a suitable solvent (e.g., benzene, toluene, hexane, dioxane or tetrahydrofuran), in the presence of a strong base (e.g., sodium hydroxide, potassium hydroxide or an aqueous solution thereof) and preferably in the presence of a phase-transfer catalyst (e.g., cetyltrimethylammonium chloride or benzyltrimethylammonium chloride) under water-containing conditions, at a temperature of −20 to +150 and preferably +20 to +100° C. If necessary, this reaction may be carried out in a sealed tube at room temperature or an elevated temperature.

Then, compound (Ib) can be obtained by reacting compound (XXVIII) with an amine (III) of the formula

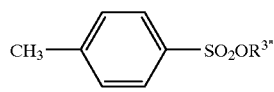

wherein the symbols are as defined previously. This reaction may be carried out in an excess of the amine or in a suitable solvent (e.g., water, methanol, ethanol, benzene, toluene, tetrahydrofuran, dimethylformamide or a mixture thereof), at a temperature of −20 to +150° C. and preferably 0 to +80° C. If necessary, this reaction may be carried out in a sealed tube at room temperature or an elevated temperature.

To take a specific example in which one of $R^3$ and $R^4$ is H and the other is alkoxy, the aforesaid starting compound (XXV) may be prepared according to the following reaction formula.

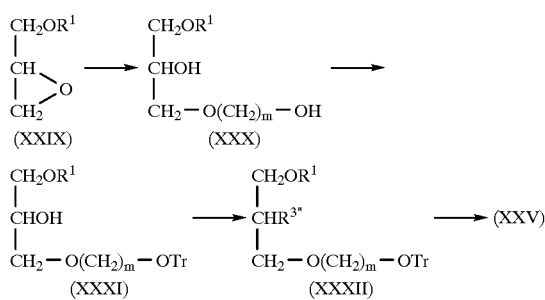

wherein Tr is trityl and the other symbols are as defined previously.

Compound (XXIX), which is the starting material for synthesis, can readily be obtained by reacting an alcohol of the general formula $R^1OH$ wherein $R^1$ is as defined previously, with epichlorohydrin in the presence of an alkali.

Compound (XXX) can be obtained by reacting compound (XXIX) with a diol of the formula $HO(CH_2)_mOH$ wherein the symbols are as defined previously. This reaction may be carried out in a suitable solvent (e.g., hexane, benzene, toluene, tetrahydrofuran, dioxane, dimethylformamide, dimethyl sulfoxide or a mixture thereof), in the presence of a strong base (e.g., sodium hydride), at a temperature of −20 to +150° C. and preferably a temperature ranging from room temperature to the reflux temperature of the solvent.

The reaction for converting compound (XXX) into compound (XXXI) is the tritylation reaction of compound (XXX). Using trityl chloride, this reaction may be carried out in a suitable solvent (e.g., benzene, toluene, dichloromethane, chloroform or pyridine), in the presence of a suitable acid accepting base (e.g., a tertiary amine such as triethylamine or pyridine), at a temperature of −20 to +150° C. and preferably 0 to +120° C.

The reaction for converting compound (XXXI) into compound (XXXII) is the alkylation reaction of compound (XXXI). Useful alkylating agents include alkyl halides ($R^{3"}$-hal wherein hal is halogen), alkyl p-toluenesulfonates of the formula and the like. This reaction may be carried out in a suitable solvent (e.g., benzene, toluene, hexane, tetrahydrofuran, dioxane, dimethylformamide, dimethyl sulfoxide or a mixture thereof), in the presence of a base (e.g., sodium hydride or an aqueous solution of sodium hydroxide) and preferably in the presence of a phase-transfer catalyst (e.g., same as described previously) under water-containing conditions, at a temperature of −20 to +150 and preferably 0 to +100° C.

A compound (XXV) can be obtained by reacting compound (XXXII) with an acid (e.g., hydrochloric acid, trifluoroacetic acid or p-toluenesulfonic acid) in a suitable water-containing solvent (e.g., methanol, ethanol, dioxane or a mixture thereof) at a temperature ranging from 10° C. to the reflux temperature, or by reacting compound (XXXII) with hydrogen chloride in chloroform at a temperature of −10 to +10° C., preferably around 0° C., and then in water-containing acetic acid at a temperature ranging from +30° C. to the reflux temperature.

Compound (XXV) may also be prepared according to the following reaction formula.

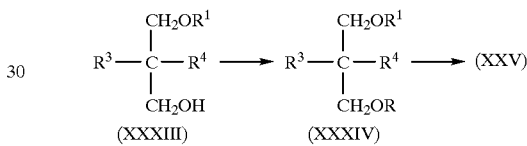

wherein the symbols are as defined previously.

The reaction for converting compound (XXXIII) into compound (XXXIV) may be carried out in substantially the same manner as described for the reaction for converting compound (XXV) into compound (XXVI), and compound (XXV) may be prepared by reacting compound (XXXIV) with a diol.

This reaction may be carried out in a suitable solvent (e.g., dimethyl sulfoxide, dimethylformamide, benzene, toluene, hexane, dioxane or tetrahydrofuran), in the presence of a strong base (e.g., sodium hydride, sodium hydroxide, potassium hydroxide or an aqueous solution thereof) and preferably in the presence of a phase-transfer catalyst (e.g., cetyltrimethylammonium chloride or benzyltrimethylammonium chloride) under water-containing conditions, at a temperature of −20 to +150° C. and preferably +20 to +100° C.

In the hair vitalizing tonic compositions of the present invention, in addition to one or more compounds of formula (I) (which may also be referred to as lipid derivatives), pharmaceutically or cosmetically acceptable vehicles and other components commonly used in hair revitalizing tonic compositions may be suitably incorporated within a range which does not impair the effects of the present invention. Examples of such components include plant extracts such as swertia herb extract and ginseng extract; vitamins such as vitamin $B_6$, vitamin E and derivatives thereof, and biotin; hair generating agents and hair generating aids such as pantothenic acid and derivatives thereof, glycyrrhizic acid and derivatives thereof, glycyrrhetic acid and derivatives thereof, nicotinic acid esters (e.g., benzyl nicotinate), cyclosporins, carpronium chloride, cepharanthine, oxendolone, diazoxide, minoxidil and ethynylestradiol; antibacterial agents such as hinokitiol, hexachlorophene, phenol, isopropylmethylphenol, benzalkonium chloride, cetylpyridinium chloride, undecylenic acid, trichlorocarbanilide and bithionol; refrigerants such as menthol and eucalyptus oil; drugs such as salicylic acid, zinc and derivatives thereof, and lactic acid and alkyl esters thereof; organic acids such as citric acid, succinic acid and malic acid; amino acids such as arginine; oil components such as silicone oil, olive oil, squalane, liquid paraffin, higher fatty acid esters (e.g., isopropyl myristate), higher fatty acids (e.g., stearic acid) and higher alcohols (e.g., cetanol); polyhydric alcohols such as glycerin, propylene glycol and 1,3-butylene glycol; surfactants such as alkylsulfates, hydrogenated castor oil ethylene oxide adduct, cocoylmethyltaurine salts, polyoxyethylene alcohol ether, fatty acid diethanolamides, ethylene glycol fatty acid esters, stearyltrimethylammonium salts and sorbitan mono-oleate; perfumes; antioxidants; edetic acid and salts thereof; ultraviolet absorbers; dyes; ethanol; water; humectants; thickeners; and preservatives.

The hair revitalizing tonic compositions of the present invention may be prepared in any dosage form that can be topically applied to the skin or hair, such as a lotion, liquid, emulsion, ointment, cream, gel and aerosol. In the preparation of these hair revitalizing tonic compositions, any of the apparatus and methods commonly used in the relevant technical field may be used to mix various ingredients and solubilize or knead the mixture. These hair revitalizing tonic compositions are used in the form of tonics, conditioners, scalp treatments, shampoos and rinses. Those skilled in the art will be able to choose the optimum combination and dosage form according to the testing methods and evaluation methods described below.

Since the compounds of the general formula (I) have very low toxicity to human beings, the present invention can provide hair revitalizing tonic compositions which are safe for human beings.

The hair revitalizing tonic compositions of the present invention may be topically applied to the skin or hair. Preferably, they are percutaneously administered by applying them directly to the skin or spraying them directly over the skin. The dosage of the hair revitalizing tonic compositions of the present invention cannot be definitely determined because they may vary with the age, individual, severity of symptoms, and the like. For human beings, however, the compounds of the general formula (I) are generally administered in a daily dose of 0.01 to 100 mg, preferably 0.1 to 50 mg, per kg of body weight. This dose may be administered once a day or in two to four divided doses.

Thus, the present invention provides hair vitalizing tonic compositions for mammals (including man) requiring a hair vitalizing treatment and, more specifically, hair vitalizing tonic compositions which are highly effective for the promotion of hair growth, the stimulation of hair growth, the prevention of hair loss, the prevention of an itchy scalp, and the prevention of dandruff, as well as a method for applying these hair vitalizing tonic compositions to mammals.

The preparation methods and hair revitalizing effects of the hair revitalizing tonic compositions of the present invention are more specifically explained with reference to the following examples. However, these examples are not to be construed to limit the scope of the present invention. In these examples, all percentages are by weight. The testing methods and evaluation methods employed in these examples are as follows.

Hair Growth Tests

Using C3H/HeNCrJ mice which were in the resting stage of a hair cycle, hair growth tests on samples were carried out according to the method of Ogawa et al. [M. Seiji and I. A. Bernstein (ed.), "Normal and Abnormal Epidermal Differentiation" (Todai Shuppan, 1982), pp. 159–170].

Specifically, mice were shaved in the back with a hair clipper and a shaver, and used in groups of ten. In test groups, 0.1 ml of each sample was applied to the mice once a day, while no sample was applied in a control group. The hair-growing effects of the samples were evaluated by measuring the area of a hair-growing part in the back of the mouse and expressing it as a percentage. The number of days required for 50% hair growth was recorded, and the data obtained with the samples were compared with those obtained with controls and, if necessary, a comparative composition. Measurements were made on the 18th, 24th, 30th, 37th and 43rd days.

EXAMPLE 1

(Preparation of a Composition in Accordance with the Present Invention)

Compound 1 of the following formula was used in this example.

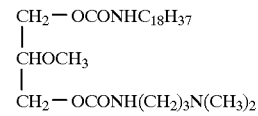

0.2 g of Compound 1, 70.0 g of 95% ethanol and 28.8 g of ion-exchanged water were mixed, and this mixture were stirred to obtain a composition.

EXAMPLES 2–11

(Compositions in Accordance with the Present Invention)

According to the procedure of Example 1, various compositions were prepared by using Compound 2, Compound 4, Compound 15, Compound 16, Compound 19, Compound 20, Compound 24, Compound 26 and Compound 27 in place of Compound 1. Moreover, a comparative composition was prepared by using croton oil in place of Compound 1. These compositions were subjected to hair growth tests. A composition to which no Compound 1 was added was used as Control 2.

The results of the hair growth tests on the compositions of Examples 1–11 and the control compositions are shown in Table II.

TABLE II

|  | Sample | Number of days required for 50% hair growth |
| --- | --- | --- |
| Comparative Example | Control 1 (no application) | 150 day or more |
| Comparative Example | Control 2 | 37 days or less |
| Example 1 | Compound 1 | 18 days or less |
| Example 2 | Compound 2 | 18 days or less |
| Example 3 | Compound 4 | 18 days or less |
| Example 4 | Compound 15 | 18 days or less |
| Example 5 | Compound 16 | 18 days or less |
| Example 6 | Compound 19 | 18 days or less |
| Example 7 | Compound 20 | 18 days or less |
| Example 8 | Compound 24 | 18 days or less |
| Example 9 | Compound 25 | 18 days or less |
| Example 10 | Compound 26 | 18 days or less |
| Example 11 | Compound 27 | 18 days or less |
| Comparative Example | Croton oil | 24 days |

As can be seen from Table II, the hair revitalizing tonic compositions of the present invention have an excellent hair growth promoting or stimulating effect. Moreover, they also exhibit a hair loss prevention effect and a dandruff and itchy scalp prevention effect.

Preparation Example 1

A lotion having the following composition was prepared.

| | |
|---|---|
| 95% ethanol | 50.0 |
| Monoammonium glycyrrhizinate | 0.1 |
| Compound 1 | 1.0 |
| Sodium lauryl sulfate | 0.1 |
| Hydrogenated castor oil ethylene oxide (40 mole) adduct | 0.5 |
| Succinic acid | q.s. |
| Perfume and dye | q.s. |
| Purified water | Balance |

(Preparation method)

Hydrogenated castor oil ethylene oxide (40 mole) adduct and a perfume were dissolved in 95% ethanol, followed by the addition of purified water. Then, other additives were added thereto and dissolved therein with stirring to obtain a clear liquid lotion.

Preparation Example 2

A lotion having the following composition was prepared.

| | |
|---|---|
| 95% ethanol | 90.0 |
| Vitamin E acetate | 0.05 |
| Compound 1 | 0.01 |
| Sodium lauryl sulfate | 0.1 |
| Propylene glycol | 0.1 |
| Hydrogenated castor oil ethylene oxide (40 mole) adduct | 0.5 |
| Lactic acid | q.s. |
| Sodium lactate | q.s. |
| Perfume and colorant | q.s. |
| Purified water | Balance |

(Preparation method)

Hydrogenated castor oil ethylene oxide (40 mole) adduct and a perfume were dissolved in 95% ethanol, followed by the addition of purified water. Then, other additives were added thereto and dissolved therein with stirring to obtain a clear liquid lotion.

The hair revitalizing tonic compositions obtained in Preparation Examples 1 and 2 had an excellent hair loss prevention and hair revitalizing effect and, moreover, an excellent dandruff and itchy scalp prevention effect.

Other Preparation Examples

The following preparations were made according to conventional procedure.

Preparation Example 3
(Hair Tonic)

| | | |
|---|---|---|
| (1) | Hinokitiol | 0.1% |
| (2) | Swertia herb extract | 1.0% |
| (3) | Vitamin $B_6$ | 0.2% |
| (4) | Vitamin E | 0.01% |
| (5) | Menthol | 0.2% |
| (6) | Salicylic acid | 0.1% |
| (7) | Compound 2 | 0.1% |
| (8) | Compound 4 | 0.001% |
| (9) | Hydrogenated castor oil ethylene oxide (40 mole) adduct | 0.1% |
| (10) | Propylene glycol | 2.0% |
| (11) | 75% ethanol | Balance |

Preparation Example 4
(Hair Tonic)

| | | |
|---|---|---|
| (1) | Hinokitiol | 0.1% |
| (2) | Swertia herb extract | 1.0% |
| (3) | Vitamin $B_6$ | 0.2% |
| (4) | Vitamin E | 0.01% |
| (5) | Menthol | 0.2% |
| (6) | Salicylic acid | 0.1% |
| (7) | Compound 3 | 1.0% |
| (8) | Compound 16 | 0.1% |
| (9) | Hydrogenated castor oil ethylene oxide (40 mole) adduct | 0.1% |
| (10) | Propylene glycol | 2.0% |
| (11) | 75% ethanol | Balance |

Preparation Example 5
(Hair Tonic)

| | | |
|---|---|---|
| (1) | Hinokitiol | 0.1% |
| (2) | Swertia herb extract | 1.0% |
| (3) | Vitamin $B_6$ | 0.2% |
| (4) | Vitamin E | 0.01% |
| (5) | Menthol | 0.2% |
| (6) | Salicylic acid | 0.1% |
| (7) | Compound 16 | 0.05% |
| (8) | Compound 20 | 0.1% |
| (9) | Hydrogenated castor oil ethylene oxide (40 mole) adduct | 0.1% |
| (10) | Propylene glycol | 2.0% |
| (11) | 75% ethanol | Balance |

Preparation Example 6
(Hair Tonic)

| | | |
|---|---|---|
| (1) | Hinokitiol | 0.1% |
| (2) | Swertia herb extract | 1.0% |
| (3) | Vitamin $B_6$ | 0.2% |
| (4) | Vitamin E | 0.01% |
| (5) | Menthol | 0.2% |
| (6) | Salicylic acid | 0.1% |
| (7) | Compound 1 | 0.1% |
| (8) | Compound 5 | 1.0% |
| (9) | Compound 6 | 0.5% |
| (10) | Compound 7 | 0.002% |
| (11) | Hydrogenated castor oil ethylene oxide (40 mole) adduct | 0.1% |
| (12) | Propylene glycol | 2.0% |
| (13) | 75% ethanol | Balance |

Preparation Example 7
(Hair Tonic)

| | | |
|---|---|---|
| (1) | Hinokitiol | 0.1% |
| (2) | Swertia herb extract | 1.0% |
| (3) | Vitamin $B_6$ | 0.2% |
| (4) | Vitamin E | 0.01% |
| (5) | Menthol | 0.2% |
| (6) | Salicylic acid | 0.1% |
| (7) | Compound 8 | 0.01 |
| (8) | Hydrogenated castor oil ethylene oxide (40 mole) adduct | 0.1% |

Preparation Example 8
(Hair Tonic)

| | | |
|---|---|---|
| (1) | Hinokitiol | 0.1% |
| (2) | Swertia herb extract | 1.0% |
| (3) | Vitamin $B_6$ | 0.2% |
| (4) | Vitamin E | 0.01% |
| (5) | Menthol | 0.2% |
| (6) | Salicylic acid | 0.1% |
| (7) | Compound 9 | 0.1% |
| (8) | Compound 25 | 0.05% |
| (9) | Hydrogenated castor oil ethylene oxide (40 mole) adduct | 0.1% |
| (10) | Propylene glycol | 2.0% |
| (11) | 75% ethanol | Balance |

-continued

| | | |
|---|---|---|
| (9) | Propylene glycol | 2.0% |
| (10) | 75% ethanol | Balance |

Preparation Example 9
(Shampoo)

| | | |
|---|---|---|
| (1) | Cocoylmethyltaurine sodium | 2.0% |
| (2) | Polyoxyethylene (8 mole) oleyl alcohol ether | 2.0% |
| (3) | Lauric acid diethanolamide | 4.0% |
| (4) | Ethylene glycol fatty acid ester | 1.0% |
| (5) | Glycerin | 0.2% |
| (6) | Menthol | 0.1% |
| (7) | Compound 10 | 0.0001% |
| (8) | Disodium edetate | 0.1% |
| (9) | Perfume | q.s. |
| (10) | Purified water | Balance |

Preparation Example 10
(Shampoo)

| | | |
|---|---|---|
| (1) | Cocoylmethyltaurine sodium | 2.0% |
| (2) | Polyoxyethylene (8 mole) oleyl alcohol ether | 2.0% |
| (3) | Lauric acid diethanolamide | 4.0% |
| (4) | Ethylene glycol fatty acid ester | 1.0% |
| (5) | Glycerin | 0.2% |
| (6) | Menthol | 0.1% |
| (7) | Compound 2 | 0.00001% |
| (8) | Disodium edetate | 0.1% |
| (9) | Perfume | q.s. |
| (10) | Purified water | Balance |

Preparation Example 11
(Shampoo)

| | | |
|---|---|---|
| (1) | Cocoylmethyltaurine sodium | 2.0% |
| (2) | Polyoxyethylene (8 mole) oleyl alcohol ether | 2.0% |
| (3) | Lauric acid diethanolamide | 4.0% |
| (4) | Ethylene glycol fatty acid ester | 1.0% |
| (5) | Glycerin | 0.2% |
| (6) | Menthol | 0.1% |
| (7) | Compound 11 | 0.001% |
| (8) | Compound 16 | 0.05% |
| (9) | Disodium Edetate | 0.1% |
| (10) | Perfume | q.s. |
| (11) | Purified water | Balance |

Preparation Example 12
(Rinse)

| | | |
|---|---|---|
| (1) | Strearyltrimethylammonium chloride | 1.5% |
| (2) | Silicone oil | 3.0% |
| (3) | Polyoxyethylene (10 mole) oleyl alcohol ether | 1.0% |
| (4) | Glycerin | 5.0% |
| (5) | Compound 1 | 0.01% |
| (6) | Preservative | q.s |
| (7) | Ultraviolet absorber | q.s. |
| (8) | Purified water | Balance |

Preparation Example 13
(Rinse)

| | | |
|---|---|---|
| (1) | Strearyltrimethylammonium chloride | 1.5% |
| (2) | Silicone oil | 3.0% |
| (3) | Polyoxyethylene (10 mole) oleyl alcohol ether | 1.0% |
| (4) | Glycerin | 5.0% |
| (5) | Compound 12 | 0.0005% |
| (6) | Compound 13 | 0.001% |
| (7) | Preservative | q.s. |
| (8) | Ultraviolet absorber | q.s. |
| (9) | Purified water | Balance |

Preparation Example 14
(Rinse)

| | | |
|---|---|---|
| (1) | Strearyltrimethylammonium chloride | 1.5% |
| (2) | Silicone oil | 3.0% |
| (3) | Polyoxyethylene (10 mole) oleyl alcohol ether | 1.0% |
| (4) | Glycerin | 5.0% |
| (5) | Compound 19 | 0.01% |
| (6) | Compound 22 | 0.001% |
| (7) | Preservative | q.s. |
| (8) | Ultraviolet absorber | q.s. |
| (9) | Purified water | Balance |

Preparation Example 15
(Rinse)

| | | |
|---|---|---|
| (1) | Strearyltrimethylammonium chloride | 1.5% |
| (2) | Silicone oil | 3.0% |
| (3) | Polyoxyethylene (10 mole) oleyl alcohol ether | 1.0% |
| (4) | Glycerin | 5.0% |
| (5) | Compound 14 | 0.001% |
| (6) | Compound 20 | 0.001% |
| (7) | Compound 23 | 0.005% |
| (8) | Preservative | q.s. |
| (9) | Ultraviolet absorber | q.s. |
| (10) | Purified water | Balance |

Preparation Example 16
(Scalp Treatment)

| | | |
|---|---|---|
| (1) | Liquid paraffin | 27.0% |
| (2) | Stearic acid | 5.0% |
| (3) | Cetanol | 5.0% |
| (4) | Sorbitan mono-oleate | 2.0% |
| (5) | Polyoxyethylene sorbitan mono-oleate | 3.0% |
| (6) | Compound 17 | 0.01% |

Preparation Example 17

(Scalp Treatment)

| | | |
|---|---|---|
| (1) | Liquid paraffin | 27.0% |
| (2) | Stearic acid | 5.0% |
| (3) | Cetanol | 5.0% |
| (4) | Sorbitan mono-oleate | 2.0% |
| (5) | Compound 18 | 0.01% |
| (6) | Compound 26 | 0.1% |
| (7) | 1, 3-Butylene glycol | 5.0% |
| (8) | Preservative | q.s. |
| (9) | Purified water | Balance |

-continued

| | | |
|---|---|---|
| (7) | Compound 24 | 0.1% |
| (8) | 1,3-Butylene glycol | 5.0% |
| (9) | Preservative | q.s. |
| (10) | Purified water | Balance |

Ingredients (5)–(7) were added to ingredients (1)–(4), and this mixture was heated at 80° C. until a homogeneous solution was obtained. The resulting solution was cooled to 30° C. and mixed with ingredients (8)–(10) to prepare a medicinal solution. The medicinal solution so prepared, together with a propellant, was packed into a container to make a scalp treatment.

The following preparations were made in substantially the same manner as described above.

Preparation Example 18

(Scalp Treatment)

| | | |
|---|---|---|
| (1) | Liquid paraffin | 27.0% |
| (2) | Stearic acid | 5.0% |
| (3) | Cetanol | 5.0% |
| (4) | Sorbitan mono-oleate | 2.0% |
| (5) | Polyoxyethylene sorbitan mono-oleate | 3.0% |
| (6) | Compound 21 | 0.005% |
| (7) | Compound 27 | 0.05% |
| (8) | 1, 3-Butylene glycol | 5.0% |
| (9) | Preservative | q.s. |
| (10) | Purified water | Balance |

Preparation Example 19

(Aerosol)

| | | |
|---|---|---|
| (Formulation for medicinal solution) | | |
| (1) | Hinokitiol | 0.1% |
| (2) | Swertia herb extract | 1.0% |
| (3) | Vitamin $B_6$ | 0.1% |
| (4) | Vitamin E | 0.01% |
| (5) | Menthol | 0.1% |
| (6) | Salicylic acid | 0.001% |
| (7) | Compound 2 | 0.1% |
| (8) | Hydrogenated castor oil ethylene oxide (40 mole) adduct | 0.1% |
| (9) | Propylene glycol | 2.0% |
| (10) | 75% ethanol | Balance |
| (Formulation for filling) | | |
| Medicinal solution | | 50.0% |
| Dimethyl ether | | 50.0% |

Preparation Example 20

(Aerosol)

| | | |
|---|---|---|
| (Formulation for medicinal solution) | | |
| (1) | Hinokitiol | 0.1% |
| (2) | Swertia herb extract | 0.5% |
| (3) | Vitamin $B_6$ | 0.1% |
| (4) | Vitamin E acetate | 0.01% |
| (5) | Menthol | 0.2% |
| (6) | Benzyl nicotinate | 0.05% |
| (7) | Compound 16 | 0.1% |
| (8) | Hydrogenated castor oil ethylene oxide (40 mole) adduct | 0.2% |
| | | 0.2% |
| (9) | Propylene glycol | 1.5% |
| (10) | 75% ethanol | Balance |
| (Formulation for filling) | | |
| Medicinal solution | | 70.0% |
| Dimethyl ether | | 30.0% |

We claim:

1. A method of promotion or stimulation of hair growth or the prevention of hair loss in a mammal which comprises topically applying an effective amount of a compound having the following formula (I), or a pharmaceutically acceptable salt thereof, to the skin or hair of a mammal requiring said method,

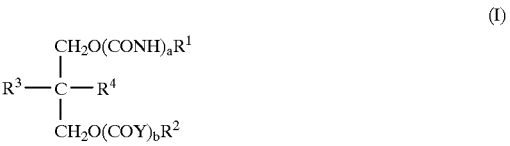

(I)

wherein $R^1$ is a straight chain or branched $C_{6-22}$ alkyl group or a $C_{6-22}$ alkyl group substituted by a $C_{3-8}$ cycloalkyl;

$R^2$ is a group of the formula

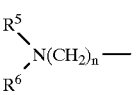

in which $R_5$ and $R^6$ are each independently hydrogen or a $C_{1-5}$ alkyl group which is optionally substituted with 1 to 5 substituents, and n is an integer of 1 to 10;

$R^3$ and $R^4$ are each independently hydrogen, hydroxyl or a $C_{1-4}$ alkoxy group;

Y is a group of the formula

wherein $R^7$ is hydrogen, a $C_{1-5}$ alkyl which is optionally substituted, a $C_{1-5}$ alkanoyl, benzoyl, phenoxycarbonyl, a $C_{1-5}$ alkoxycarbonyl, a $C_{1-5}$ alkylcarbamoyl which is optionally substituted, a di-$C_{1-5}$ alkyl carbamoyl which is optionally substituted or a 3 to 7 membered cyclic aminocarbonyl which is optionally substituted;

a is 0 or 1; and b is 0 or 1.

2. The method as claimed in claim 1, wherein $R^1$ is a $C_{6-14}$ alkyl group substituted by a $C_{5-6}$ cycloalkyl group, or a straight chain or branched $C_{8-20}$ alkyl group;

$R^2$ is a group of the formula

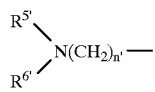

in which $R^{5'}$ and $R^{6'}$ are each independently methyl or ethyl, and n' is an integer of 2 to 6, $R^3$ and $R^4$ are each independently hydrogen or methoxy, and Y is an imino group.

3. The method as claimed in claim 1, wherein when $R^5$ or $R^6$ are a $C_{1-5}$ alkyl group which is substituted with 1 to 5 substituents, the substituents are selected from the group consisting of $C_{3-8}$ cycloalkyl, hydroxyl, oxo, thioxo, cyano, carbamoyl, carboxyl, $C_{1-4}$ alkoxycarbonyl, sulfo, halogen, $C_{1-4}$ alkoxy, phenoxy, halogenophenoxy, $C_{1-4}$ alkylthio, phenylthio, $C_{1-4}$ alkylsulfinyl, $C_{14}$ alkylsulfonyl and $C_{1-10}$ haloalkyl.

4. The method as claimed in claim 1, wherein $R^7$ is a $C_{1-5}$ alkyl group which is substituted with a carboxyl or a $C_{1-5}$ alkoxycarbonyl.

5. The method as claimed in claim 1, wherein $R^1$ is a $C_{12}$ alkyl group substituted by a $C_6$ cycloalkyl group at the ω-position or $C_{18}$ alkyl group, $R^2$ is a group of the formula

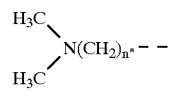

in which
n" is an integer of 2 to 4,
$R^3$ and $R^4$ are each independently hydrogen or methoxy.

6. The method as claimed in claim 5, wherein a and b are both 1.

7. The method of claim 1, wherein the compound is

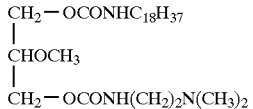

or a salt thereof.

8. The method as claimed in claim 1, wherein the compound is applied together with a pharmaceutically or cosmetically acceptable vehicle.

9. A method of promotion or stimulation of hair growth or the prevention of hair loss in a mammal which comprises topically applying an effective amount of a compound:

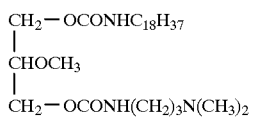

or a pharmaceutically acceptable salt thereof, to the skin or hair of a mammal requiring said method.

* * * * *